United States Patent [19]

Horowitz et al.

[11] Patent Number: 5,120,649

[45] Date of Patent: Jun. 9, 1992

[54] PHOTODYNAMIC INACTIVATION OF VIRUSES IN BLOOD CELL-CONTAINING COMPOSITIONS

[75] Inventors: Bernard Horowitz, New Rochelle; Jay E. Valinsky; Nicholas E. Geacintov, both of New York; Bolanle Williams, Forest Hills; Shanti B. Rywkin, Brooklyn, all of N.Y.

[73] Assignee: New York Blood Center, Inc., New York, N.Y.

[21] Appl. No.: 524,208

[22] Filed: May 15, 1990

[51] Int. Cl.$^5$ ............... C12N 13/00; C12N 7/04; A61K 39/36

[52] U.S. Cl. ............... 435/173; 435/236; 424/90

[58] Field of Search ............ 435/173, 236; 424/90

[56] References Cited

U.S. PATENT DOCUMENTS

| | | | |
|---|---|---|---|
| 4,008,136 | 2/1977 | Williams | 204/158 R |
| 4,530,924 | 7/1985 | Polony et al. | 514/191 |
| 4,693,981 | 9/1987 | Wiesehahn et al. | 435/238 |
| 4,775,625 | 10/1988 | Sieber | 435/238 |
| 4,878,891 | 11/1989 | Judy et al. | 604/5 |
| 4,935,498 | 6/1990 | Sessler | 534/15 |

OTHER PUBLICATIONS

Morgan et al., (1989) *Br. J. Lancer,* 59(3), 366–70 (Abstract).

Snipes et al., (1977) *Radiat. Res.,* 70(3), 667, conference.

J. Morgan, A. G. Gray & E. R. Huehns, "Phthalocyanine Photosensitised Liposomes Directed to Cells by Monoclonal Antibody In Vitro".

H. S. Neyndorff et al., "Development of a Model to Demonstrate Photosensitizer-Mediated Viral Inactivation in Blood".

*Primary Examiner*—David M. Naff
*Assistant Examiner*—Jon P. Weber
*Attorney, Agent, or Firm*—Sprung Horn Kramer & Woods

[57] ABSTRACT

The present invention concerns a method of inactivating extracelluar lipid enveloped human pathogenic virus or intracelular human pathogenic virus in a blood cell-containing composition without incurring substantial disruption or inactivation of cells, comprising contacting a cell-containing composition having $\geq 1 \times 10^9$ cells/ml and containing infectious virus with a virucidally effective amount of at least one photoreactive compound having an absorption maximum of $\geq 630$ nm, light and an oxidizer to substantially inactivate the virus to effect a virus kill of at least $10^4$ and to result in a retention of intact cell functionality and structure of greater than 80%. The present invention also is directed to a composition comprising human red blood cells suitable for transfusion at a concentration of $\geq 1 \times 10^9$ cells/ml and having all extracellular lipid enveloped and intracellular human pathogenic viruses in a noninfectious form.

21 Claims, 3 Drawing Sheets

PHOTODYNAMIC INACTIVATION OF VIRUSES IN BLOOD CELL-CONTAINING COMPOSITIONS

GOVERNMENT RIGHTS

This invention was made with United States government support under Grant 1-RO1-HL41221 from the NHLBI. The United States Government has certain rights in this invention.

This invention was made with United States government support under Grant HL41221 from the NIH. The United States Government has certain rights in this invention.

BACKGROUND OF THE INVENTION

1. Field of the Invention

The present invention concerns a method to inactivate viruses in cell-containing compositions, for example, in whole blood or red blood cell concentrates, without incurring substantial disruption or inactivation of cells, for example, without adversely affecting red blood cell structure or function, by using a photoactive compound, for example, a phthalocyanine, together with light exposure.

2. Description of Related Art

Nature of the Concept

Substantial progress has been made in reducing the viral infectivity of whole blood and its components through improved donor selection and donor blood screening procedures. Despite this progress, there is a continued risk of transmission of viruses including hepatitis viruses and human immunodeficiency viruses (HIV) by whole blood and blood products.

Viral risk has been considerably reduced and possibly eliminated in coagulation factor concentrates through the application of virucidal procedures during the course of manufacture (Prince, A. M., Horowitz, B., Horowitz, M. S., Zang, E., "The Development of Virus-Free Labile Blood Derivatives–A Review", *Eur. J. Eoidemiol.*, 1987;3:103–118 and Mannucci, P. M., Colombo, M., "Virucidal Treatment of Clotting Factor Concentrates", *The Lancet*, 1988;782–785). By contrast, the development of virucidal processes applicable to cell components, i.e., blood cell fractions such as red blood cells or platelets, has been slow, both because cells are more fragile than proteins, and cells serve to harbor and protect virus against inactivation. Nonetheless, if virus transmission by whole blood or blood components is to be eliminated, effective virus removal or potent virucidal methods applicable to blood cells will be required. Since both red blood cells or platelets are non-replicating, approaches directed toward nucleic acid modification might offer the required specificity.

It is important to recognize in assessing virucidal procedures that virus will be present in cell-containing solutions in multiple forms: virus free of the cell; formed virus associated with the cell; functional, but unpackaged viral nucleic acid within the cell; and viral nucleic acid integrated into the cell genome. Each form should be considered infectious and capable of causing viral disease in vivo. Virucidal methods which inactivate virus in one form, e.g., cell-free virus, may not inactivate virus in other forms, e.g., cell-associated forms. Additionally, the presence of cells is known to inhibit the action of both physical and chemical approaches to virus inactivation. Cells compete for added virucidal reagents and absorb radiation which otherwise would be virucidal. Thus, for example, while ultraviolet irradiation is highly virucidal in salt solutions or in dilute protein solution, the degree of virucidal activity is incomplete when treating cell-containing solutions. Furthermore, in this context, it is not sufficient to inactivate virus alone; rather, it is necessary to do so with sufficient vigor that viral infectivity is eliminated without deleterious effects to the valuable cell components, e.g., red blood cells.

Most virucidal procedures which have been developed, e.g., pasteurization or solvent/detergent treatment, cannot be applied to blood cell preparations without damaging the cells and rendering them unfit for transfusion.

Heretofore, it has not been possible to prepare virus sterilized forms of whole blood or red cell concentrates or platelet concentrates where at least $10^4$ infectious units ($ID_{50}$) and preferably $\geq 10^6$ $ID_{50}$ of both intracellular and extracellular virus were inactivated without adversely affecting the cells and/or without using highly toxic agents.

Phthalocyanines

While there has been growing interest in the use of phthalocyanines for the treatment of cancerous cells (Rosenthal, I. and Ben Hur, E., "Phthalocyanines in Photobiology", Lezhoff C. C. and Lever A. B. P. eds., *Phthalocyanines*, VCH Publishers, Inc., New York, New York, 1989, 393–425), phthalocyanines are generally thought of as being hemolytic, making applicants' results herein all the more surprising. For example, Ben-Hur and Rosenthal ("Photohemolysis of Human Erthrocytes Induced by Aluminum Phthalocyanine Tetrasulfonate", *Cancer Lett.*, 30: 321–327, 1986) studied the photohemolysis of human red blood cells induced by aluminum phthalocyanine tetrasulfonate. Substantial (20%–100%) hemolysis was induced by treatment with 2.5 to 10 μM $AlPcS_4$ at all light fluences $\geq 40$ $KJ/m^2$ ($\geq 4$ $J/cm^2$). Ben-Hur and Rosenthal did not address the problem of virus kill. Similarly, Sonoda, Krishna and Riesz ("The Role of Singlet Oxygen in the Photohemolysis of Red Blood Cells Sensitized by Phthalocyanine", *Photochem. Photobiol.*, 46: 625–631, 1987) studied the photohemolysis induced by each of several phthalocyanine derivatives. Aluminum and zinc phthalocyanines were each hemolytic, while free (no metal) phthalocyanine or those with iron, copper or cobalt as the central metal cation were not. Virus kill was not studied.

Singer et al (C. R. J. Singer, T. Azim and Q. Sattentau, "Preliminary Evaluation of Phthalocyanine Photosensitization For Inactivation Of Viral Pathogens in Blood Products", [abstract] *British J. Hematology*, Mar. 23–25, 1988:Abs. 31), in what is believed to be the only study on virus kill performed with phthalocyanines, demonstrated that an unstated quantity of both Epstein Barr virus and of HIV added to plasma was inactivated on treatment with 5 and 1 25 μg/mL of sulfonated aluminum phthalocyanine and $2mW/cm^2$ for 30 minutes (3.6 $J/cm^2$). Factor VIII recovery was only 50%. Singer et al reported no actual work on cells or cell-associated virus, though they state that application to red cells is being evaluated. Given the relatively poor recovery (50%) of factor VIII reported by Singer, the greater fragility of cells than proteins, and the previous experience on the photohemolysis of red cells to treatment with phthalocyanine, the results herein are all the more surprising.

Other Lipophilic Dyes in the Treatment of Whole Blood or Red Blood Cell Concentrates Cole et al (Cole, M., Stromberg, R., Friedman, L., Benade, L., Shumaker, J., "Photochemical Inactivation of Virus in Red Cells", *Transfusion*, 29, Supp:42s Abs., 1989) explored the use of merocyanine 540 in the treatment of packed red blood cells diluted to a hematocrit of 15%. When plasma was removed such that its concentration was 2.6%, a 6 log reduction of vesicular stomatitis virus was achieved. However, only a 1 log reduction in VSV was achieved in samples containing 15% plasma. The authors concluded that "although plasma is required to protect the red blood cells from damage, viral kill is also significantly reduced". This conclusion is supported by the observation that the presence of 5% albumin inhibited virus kill in suspension of washed platelets (Prodouz, K. N., "Effect of Merocyanine 540 on Platelet Function and Reduction of its Antiviral Activity by Albumin", *Transfusion*, 29, Supp:42s Abs., 1989), and that though 6 logs of model viruses in buffer could be inactivated by merocyanine 540, only 1-3 logs of virus could be inactivated in the presence of 12%-25% plasma (Moroff, G., Benade, L. E., Dabay, M., George, V. M., Shumaker, J. and Dodd, R. Y., "Use of Photochemical Procedures to Inactivate Viruses in Platelet Suspensions", *Transfusion*, 29, Supp:S15 Abs., 1989). Furthermore, the authors stated that the procedure "adversely affected platelet properties".

Matthews, J. T., Newman, J. T., Sogandares-Bernal, F., et al, "Photodynamic Therapy of Viral Contaminants with Potential For Blood Banking Applications", *Transfusion*, 1988;28:81-83 studied treatment of whole blood with hematoporphyrin derivatives and light. They reported the inactivation of $3 \times 10^5$ PFU of herpes simplex virus type 1 (HSV-1) on treatment of culture medium with 2.5 µg/mL dihematoporphyrin ether (DHE) and light, but only the inactivation of $10^3$ PFU on treatment of blood under the same condition. Increasing the concentration of DHE to 20 µg/ml did not improve virus kill. While red blood cell structure and function was well maintained at 2.5 µg/mL DHE and light at 5 J/cm$^2$, cell-free HIV ($2 \times 10^3$ ID$_{50}$) added to buffer alone was not completely killed under this condition.

Other Agents

Lin et al (Lin, L., Wiesehahn, G. P., Morel, P. A. and Corash, L., "Use of 8-Methoxypsoralen and Long-wavelength Ultraviolet Radiation for Decontamination of Platelet Concentrates", *Blood*, 74:517-525, 1989) demonstrated that psoralen and exposure to UV-A inactivated $\geq 10^{5.5}$ID of feline leukemia virus added to a platelet concentrate; however, studies in whole blood or red cell concentrates were not performed. Platelet morphology, aggregation, and the release reaction were well maintained immediately following treatment, and showed comparable values when compared to untreated controls on storage for up to 96 hours. In contrast, Moroff et al (Moroff G., Benade, L. E., Dabay, M., George, V. M., Shumaker, J. and Dodd, R. Y., "Use of Photochemical Procedures to Inactivate Viruses in Platelet Suspensions", *Transfusion*, 29, Supp. S15 Abs., 1989) explored the use of psoralen for the treatment of platelets and concluded that the presence of as little as 12% plasma inhibited virus kill and that platelet properties were adversely affected. It should be pointed out that, as typically prepared, red blood cells and platelet concentrates for transfusion are suspended in 100% plasma.

In U.S. patent application Ser. No. 07/279,179, filed Dec. 2, 1988, and in a recent published abstract (Williams et al, *Blood*, 1988, 72:Suppl.:287a), vesicular stomatitis virus added to whole blood was reported to be inactivated on incubation with a hydrolyzable, aryl diol epoxide without causing red cell lysis.

Ozone has been asserted to decontaminate whole blood containing $10^9$ pFU/mL of hepatitis virus (Zee, Y. C. and Bolton, D. C., "Ozone Decontamination of Blood and Blood Products", U.S. Pat. No. 4,632,980). However, no data were provided in support of this allegation.

Prodouz, K. N., Fratantoni, J. C., Boone, J. E. and Bonner R. F., "Use of Laser-UV for Inactivation of Virus in Blood Products", *Blood*, 1987; 70:589-592 reported that laser-UV treatment of a platelet concentrate largely maintained platelet function under conditions where up to $10^6$ (ID$_{50}$) of polio virus was inactivated. However, virus inactivation was studied in buffered medium alone and not in the presence of platelets, and only a cell-free form of the virus was employed.

Hartman et al (Hartman, F. W., Mangun, G. H., Feeley, N., Jackson, E., "On the Chemical Sterilization of Blood and Blood Products", *Proc. Soc. Exp. Biol. Med.*, 70:248-254, 1949) showed that treatment of whole blood with the nitrogen mustard, methyl-bis(beta-chloroethyl) amine hydrochloride resulted in the inactivation of $10^{6.6}$ ID$_{50}$ of vesicular stomatitis virus under conditions where red cell hemolysis was not greater than the control. It should be pointed out that nitrogen mustards are carcinogens.

LoGrippo (LoGrippo, G. A., "Investigations of the Use of Beta-Propiolactone in Virus Inactivation", *Ann. NY Aca. Sci.*, 83, 578-594, (1959)) treated red cells separately from plasma with beta-propiolactone. Treatment resulted in the inactivation of more than $10^8$ ID$_{50}$ of Eastern equine encephalitis virus without causing red cells in man resulted in a shortened circulatory half-life.

SUMMARY OF THE INVENTION

It is an object of the present invention to inactivate viruses in cell-containing compositions without incurring substantial disruption or inactivation of cells.

It is another object of the present invention to inactivate viruses in whole blood, red blood cell concentrates and platelet concentrates, without adversely affecting red cell or platelet structure or function.

It is a further object of this invention to improve virus safety in blood banks of both whole blood, red blood cell concentrates and platelet concentrates, and any products derived from whole blood, red blood cell concentrates or platelet concentrates.

It is still a further object of the invention to reduce exposure to hospital care workers and other health care workers to viruses to which they otherwise would be exposed.

It is still a further object of the invention to reduce the circulating viral burden in animals and man.

It is still a further object of the invention to improve the storage properties of cell-containing compositions, e.g., red cell concentrate, prior to use.

The above objects, as well as other objects, aims and advantages are satisfied by the present invention.

The present invention concerns a method of inactivating excellular lipid enveloped human pathogenic viruses or intracellular human pathogenic viruses in a cell-containing composition without incurring substantial disruption or inactivation of cells, comprising contacting a cell-containing composition having $\geq 1 \times 10^9$ cells/ml and containing infectious virus with a virucidally effective amount of at least one photoreactive compound having an absorption maximum of $\geq 630$ nm, light and an oxidizer to substantially inactivate the virus and to result in a retention of intact cell functionality and structure of greater than 80%.

More particularly, the present invention concerns a method for inactivating extracellular lipid enveloped viruses, as well as intracellular viruses, in whole blood, red blood cell concentrates, platelet concentrates or products derived from whole blood or red blood cell concentrates or platelet concentrates comprising contacting said whole blood, red blood cell concentrates or products derived from whole blood or red blood cell concentrates with an effective virucidal amount of a photoreactive compound having an absorption maximum greater than 630 nm, for example, a purpurin or a phthalocyanine, and exposing the resultant composition to light in the presence of an oxidizer.

The present invention also concerns a composition comprising human red blood cells suitable for transfusion at concentration of $\geq 1$ to $10^9$ cells/ml and having all extracellular lipid enveloped and intracellular human pathogenic viruses in a non-infectious form, the red cells preferably having a normal recovery on infusion of 70% or greater, preferably 85% or greater and having a satisfactory circulatory survival, e.g., for red blood cells of $\geq 20$ days and preferably for 30 days.

The aforesaid compositions preferably have a greater resistance to osmotic shock than normal.

BRIEF DESCRIPTION OF THE DRAWINGS

FIG. 1 comprises four graphs depicting the inactivation of cell-free vesicular stomatitis virus (VSV) with aluminum phthalocyanine chloride (AlPc). FIG. 1a depicts the results using whole blood. FIG. 1b depicts the results using a red blood cell concentrate. FIG. 1c depicts the results using whole blood diluted 5-fold with PBS. FIG. 1d depicts the results using a red blood cell concentrate diluted 2-fold with PBS.

FIG. 2 comprises four graphs depicting the inactivation of cell-free VSV with sulfonated aluminum phthalocyanine.

DETAILED DESCRIPTION OF THE INVENTION

Figure 2A:
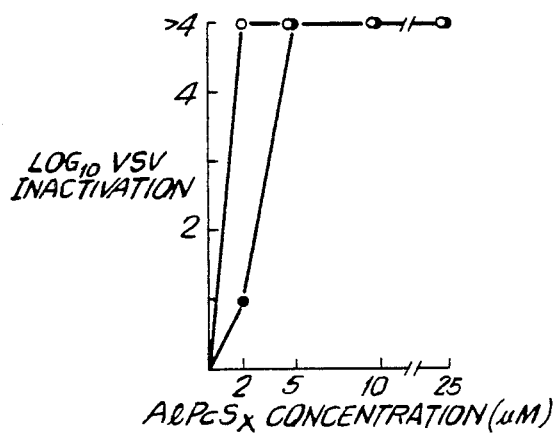
FIG. 2a depicts the results using AlPcS$_2$ with whole blood.

Blood is made up of solids (cells, i.e., erythrocytes, leucocytes, and platelets) and liquid (plasma). The cells are transfused in the treatment of anemia, clotting disorders, infections, etc. In addition, the cells contain potentially valuable substances such as hemoglobin, and they can be induced to make other potentially valuable substances such as interferon, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the cells and/or proteins to be concentrated, thus enhancing their therapeutic use.

Cell types found in human blood include red blood cells, platelets and several types of leukocytes. Methods for the preparation of cell concentrates useful in transfusion can be found in *Kirk Othmer's Encyclopedia of Chemical Technology*, Third Edition, Interscience Publishers, Volume 4, pp 25-37, the entire contents of which are incorporated by reference herein.

Proteins found in the blood cell fraction include hemoglobin, fibronectin, fibrinogen, platelet derived growth factor, superoxide dismutase, enzymes of carbohydrate and protein metabolism, etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Academic Press, New York, (1979).

The present invention is directed to contacting at least one photoreactive compound with a cell-containing composition such as whole blood, red blood cell concentrates, platelet concentrates, platelet extracts, leukocyte concentrates, semen, ascites fluid, milk, lymphatic fluid, hybridoma cell lines and products derived from any of the above.

The present invention can be employed to treat the product of a composition containing a non-blood normal or cancerous cells or the product of gene splicing.

Suitable photosensitizer compounds for use in the present invention include phthalocyanines, purpurins and other molecules which resemble the porphyrins in structure, although some of the atoms in the basic porphyrin-like frame (as well as their arrangement) may vary. For example, phthalocyanines are porphyrin-like (azaporphyrins), except that the tetrapyrrole ring linked by methine carbon atoms in porphyrins is replaced by four isoindole units linked by aza nitrogen atoms. These phthalocyanine, porphyrin, and purpurin molecules may or may not contain metallo or metalloid central atoms, and various substituents may be placed on the basic molecular framework to (a) red-shift the longest wavelength absorption maxima beyond 630 nm, (b) increase the molar extinction coefficient to enhance the absorptivity of the exciting red light, and (c) modulate the solubilities of the photosensitizer molecules in aqueous environments, as well as their lipophilicities, or DNA-binding abilities.

Photoreactive compounds for use in the present invention which contain metals, for example, germanium or gallium, are diamagnetic, rather than paramagnetic.

Photosensitizers, including substituted photosensitizers, which can be utilized in the present invention will result in compounds having the following characteristics:

(a) a molar extinction coefficient of $\geq 50,000$ Molar$^{-1}$ cm$^1$;

(b) an absorption maximum of $\geq 630$ nm, preferably 660 to 730;

(c) a solubility of $\geq 1$ $\mu$M in both water and apolar solvents;

(d) having amphiphilic characteristics;

(e) soluble in aqueous saline buffer solutions at the concentrations of use in a time frame of approximately 2 hours.

Preferred photoreactive compounds for use in the present invention are phthalocyanines (Pc's or PC's). Phthalocyanines are porphyrin-like compounds which are chemically stable, well defined, and easily synthesized (Spikes, J., "Phthalocyanines as Photosensitizers in Biological Systems and for the Photodynamic Therapy of Tumors", *Photochemistry and Photobiology*, 1986;43:691-699 and Ben-Hur, E. and Rosenthal, I.,"- The Phthalocyanines: A New Class of Mammalian Cells Photosensitizers with a Potential for Cancer Phototherapy", *Int. J. Radiat. Biol.*, 1989;47:145-147). There is encouraging evidence in the literature indicating the lack of toxicity of phthalocyanine dyes to mammals (Moser, F. H. and Thomas, A. C., *The Phthalocyanines*, Boca Raton:CRC Press, 1984). The phthalocyanines have very strong electronic absorption bands at wavelengths above 630 nm. Hemoglobin has a relatively low absorbance in this spectral region.

Non-limiting examples of phthalocyanines for use in the present invention include the following:
zinc tetrasulfophthalocyanine,
tetrasulfophthalocyanine,
aluminum tetranitrophthalocyanine,
zinc-tetranitrophthalocycyanine,
tetracarboxyphthalocyanine,
GaCl-tetrasulfophthalocyanine,
AlCl-tetrasulfophthalocyanine,
Ga-tetrasulfophthalocyanine and
GaCl-, AlCl- or Ga-tetranitrophthalocyanine.

In a preferred embodiment of the invention, aluminum phthalocyanines are employed. Preferred aluminum phthalocyanines include aluminum phthalocyanine chloride (AlPc) and sulfonated forms of aluminum phthalocyanine, e.g., AlPcS$_2$ and AlPcS$_4$. Zinc can replace aluminum as the central atom, and the ring can be nitrated instead of sulfonated.

Non-limiting examples of lipid coated, human pathogenic viruses that can be inactivated by the present invention include vesicular stomatitis virus (VSV), Moloney sarcoma virus, Sindbis virus, human immunodeficiency viruses (HIV-1; HIV-2), human T-cell lymphotrophic virus-I (HTLV-I), hepatitis B virus, non-A, non-B hepatitis virus (NANB) (hepatitis C), cytomegalovirus, Epstein Barr viruses, lactate dehydrogenase elevating virus, herpes group viruses, rhabdoviruses, leukoviruses, myxoviruses, alphaviruses, Arboviruses (group B), paramyxoviruses, arenaviruses and coronaviruses.

The process of the present invention is preferably conducted at 0° C. to 45° C., and most preferably at 4° C. to 37° C. for up to 48 hours and preferably for 2 to 24 hours.

The process of the invention is preferably conducted in a neutral pH range of 6.3 to 7.7. A typical light fluence range for the invention is 10 to 1000 J/cm$^2$, preferably 100 to 600 J/cm$^2$. The brighter the light, the less time is required. With flowing systems, very bright light for short times would be employed. For blood bags, longer times and less bright light can be used.

Preferably the concentration of the photoreactive compound is 1 to 25 $\mu$M; for red cell concentrates, the concentration of the photoreactive compound is most preferably 10 to 25 $\mu$M.

The process of the present invention is carried out in the presence of an oxidizer. Oxygen is a non-limiting example of an oxidizer for use in the present invention. The concentration of oxygen can be the endogenous quantity, or can be modified by placement of the material being treated in an atmosphere designed to lower or raise oxygen concentration.

Cell-containing compositions to be treated according to the invention have $\geq 1 \times 10^9$ cells/ml, preferably $\geq 5 \times 10^9$ cells/ml and most preferably $\geq 1 \times 10^{10}$ cells/ml. Furthermore, cell-containing compositions to be treated according to the invention have preferably $>4$ mg/ml protein and more preferably $>25$ mg/ml protein and most preferably 50 to 60 mg/ml protein (unwashed cells).

In the inventive process, at least $10^4$, preferably $10^6$, infectious units of virus are inactivated.

The inventive process results in improved storage stability, i.e., treated cells that can be stored in liquid or frozen form and for which reduced cell destruction is obtained.

The cell-containing composition according to the invention, while initially containing $\geq 1000$ infectious units of virus/L, after the virus has been inactivated and treatment according to the invention has been conducted, has a retention of intact cell functionality and structure of greater than 80%, preferably greater than 90% and most preferably greater than 98%.

By the inactivation procedure of the invention, most if not virtually all of the viruses contained therein would be inactivated. A method for determining infectivity levels by inoculation into chimpanzees (in vivo) is discussed by Prince, A. M., Stephen, W., Bortman, B. and van den Ende, M. C., "Evaluation of the Effect of Betapropiolactone/Ultraviolet Irradiation (BPL/UV) Treatment of Source Plasma on Hepatitis Transmission by Factor IX Complex in Chimpanzees", *Thrombosis and Hemostasis*, 44: 138-142, (1980).

According to the invention, inactivation of virus is obtained to the extent of at least "4 logs", preferably $\geq 6$ logs, i.e., virus in the sample is totally inactivated to the extent determined by infectivity studies where that virus is present in the untreated sample in such a concentration that even after dilution to $10^4$ (or $10^6$), viral activity can be measured.

The present invention describes inactivating viruses, while simultaneously retaining labile blood cell functional and structural features.

Functional activities of red cells are ascertained by measurements of metabolite levels, enzymatic activities, electrolyte levels and oxygen carrying capacity. Structural integrity of red cells is assessed by measurements of hemoglobin release, osmotic fragility, survival in vivo following radiolabeling with chromium-51, antigenicity and by evaluation of modification of cell surface proteins.

Functional activities of platelets are determined by their ability to aggregate in the presence of certain biological agents and their morphology. Structural integrity of platelets is assessed by in vivo survival following radiolabeling with indium-111 and identification of the presence of specific platelet antigens.

The method of the present invention can be used in conjunction with other viral inactivating agents, e.g., beta-propiolactone or UV or other forms of radiation, e.g., gamma rays.

The present invention demonstrates the following:

(1) photoreactive compounds such as phthalocyanines together with light exposure can inactivate viruses in whole blood or red cell concentrates, without adversely affecting red cell structure or function, (2) a lipophilic dye with an absorption maximum of $\geq 630$ nm can inactivate large quantities (e.g., $\geq 10^4$ IDD$_{50}$) of virus in whole blood or a red cell concentrate under conditions which maintain red cell structure and function, (3) both extracellular and intracellular virus present in whole blood, a red cell concentrate or a platelet concentrate can be inactivated without adversely affecting cell structure or function, and (4) a lipophilic dye on exposure to light can stabilize red blood cells to osmotic injury.

The principal advantage of the phthalocyanines over other lipophilic dyes such as hematoporphyrin derivative is the extremely strong optical absorption of phthalocyanines at 630-700 nm. Light at this wavelenqth has improved tissue penetrating properties, as compared with the shorter wavelength of light absorbed by the usual porphyrin and hematoporphyrin sensitizers. Furthermore, the absorption spectrum of phthalocyanines is better separated from that of blood components, especially hemoglobin, which has an absorption maximum at 578 nm.

Photodynamic action appears to require both the presence of light and an oxidizing agent, e.g., oxygen.

The detailed mechanism of the action of dyes such as hematoporphyrin derivative or phthalocyanine is unknown (Foote, C. S., "Mechanisms of Photooxygenation". In: Doiron D. R., Gomer C. J. eds., *Porphyrin Localization and Treatment of Tumors*, Proceedings of the Clayton Foundation International Symposium, New York: Alan R. Liss, Inc., 1983:3-18; Ben-Hur, E., Carmichael A., Riesz, P. and Rosenthal, I., "Photochemical Generation of Superoxide Radical and the Cytotoxicity of Phthalocyanines", *Int. J. Radiat. Biol.*, 1985;48:837-846; Ben-Hur, E. and Rosenthal, I., "Photohemolysis of Human Erythrocytes Induced by Aluminum Phthalocyanine Tetrasulfonate", *Cancer Letters*, 1986;30:321-327 and Sonoda, M., Krishna, C. M., and Riesz P., "The Role of Singlet Oxygen in the Photohemolysis of Red Blood Cells Sensitized by Phthalocyanine Sulfonates", *Photochemistry and Photobiology*, 1987;46:625-631). However, without wishing to be bound by any particular theory of operability, it appears likely that these bind to membranes, e.g., lipid enveloped viruses or cell membranes and, on exposure to light, result in the production of reactive, singlet oxygen species (Ben-Hur et al, *Cancer Letters*, 1986;30:321-327). It has been suggested that the above results in nucleic acid damage (Ben-Hur, E. and Rosenthal, I., "Factors Affecting the Photokilling of Cultured Chinese Hamster Cells by Phthalocyanines", *Radiation Research*. 1985;103:403-409). In this manner, any intracellular virus would be inactivated, whether or not it is lipid-enveloped, when inside the cell.

As reported herein, extracellular enveloped viruses such as VSV and HIV were inactivated, while extracellular encephalomyocarditis virus (EMC), a non-enveloped virus, was not. In addition, AlPcS$_2$ and AlPcS$_4$, which bind to the more hydrophilic regions of the cell, were more effective virucidal agents than AlPc at a similar concentration. It is important to note that both cell-free and cell-associated viruses were inactivated under the conditions examined, and that red cell integrity was maintained, as judged by the absence of hemoglobin release ($<2\%$) on treatment, or following storage. In fact, treatment of a red cell suspension with AlPc and light stabilized the red cell against hypotonic shock.

That VSV added to an entire red blood cell concentrate unit was inactivated indicates that a procedure based on AlPc addition and exposure to light can be implemented in a blood banking environment. Treatment of collected units in a light cabinet, perhaps for a period as long as 6 to 24 hours, or for briefer periods if multiple or more intense light sources are employed, is envisioned.

In a preferred embodiment of the present invention, a light fluence of 250 to 1000 J/cm$^2$ is applied to a sample 2 to 4 cm thick and agitation is utilized. In a further preferred embodiment of the invention, the process according to the invention is applied to a sample in a blood bag.

After treatment with the photoreactive compound, excess photoreactive compound can be removed by centrifugation, washing and/or dialysis.

In an embodiment of the present invention, the treated cell-containing fraction from the inventive process is transfused or returned to the donor, e.g., human donor, from which the initial cell-containing fraction was derived. In this manner, the level of circulating virus in the donor will be reduced, thus improving the donor's ability to clear virus and/or improving the efficacy of antiviral drugs.

The invention will now be described with reference to the following non-limiting examples.

EXAMPLES

Materials and Methods

Blood

Whole blood was typically less than 48 hours old when used. Prior to use, it was stored at 4° C. Red blood cell concentrates (RBCC) were prepared from whole blood by centrifugation for 20 minutes at 2000 r.p.m. with removal of most of the plasma layer. Where indicated, whole blood was diluted 5-fold or the red blood cell concentrates were diluted 2-fold with phosphate buffered saline (PBS; Gibco Laboratories, Grand Island, New York).

Aluminum Phthalocyanine Solutions

Aluminum phthalocyanine chloride (AlPc) was purchased from Kodak Laboratory Chemicals, Rochester, New York. Stock solutions of AlPc (0.01 M) were prepared in spectrophotometric grade N,N-dimethylformamide (Aldrich, Milwaukee, Wisconsin). Aluminum phthalocyanine tetrasulfonate (AlPcS$_4$) and aluminum phthalocyanine disulfonate (AlPcS$_2$) were purchased from Porphyrin Products Inc., Logan, Utah. Stock solutions of AlPcS$_2$ and AlPcS$_4$ ($6.2 \times 10^{-4}$ M) were prepared in PBS. The concentration of all phthalocyanine solutions was determined spectrophotometrically using a molar extinction coefficient of $2 \times 10^5$ 1 mol$^{-1}$ cm$^{-1}$ at the absorption maximum at 670 nm for AlPc, 674 nm for AlPcS$_2$ and 675 nm for AlPcS$_4$.

Model Virus Studies

The inactivation of the following viruses was studied: vesicular stomatitis virus (VSV), a lipid enveloped, RNA virus; encephalomyocarditis virus (EMC), a protein enveloped, RNA virus; and human immunodeficiency virus (HIV), a human, pathogenic retrovirus.

VSV was cultured in human A549 cells. EMC stocks were prepared in mouse L929 or human A459 cells. Culturing and assay procedures were similar to those described in Horowitz, B., Wiebe, M. E., Lippin, A. and Stryker, M. H., "Inactivation of Viruses in Labile Blood Derivatives", *Transfusion*, 1985;25:516-522. Infectivity of VSV and EMC was assessed by endpoint, 10-fold serial dilutions in DMEM culture medium (Gibco Laboratories, Grand Island, New York) with 10% fetal calf serum (FCS; MA Bioproducts, Walkersville, Maryland). Each dilution was used to inoculate eight replicate wells of human A549 cells in 96-well microtiter plates. Virus-induced cytopathology was scored after 72 hours of incubation at 37° C. in 5% $CO_2$. The reported virus titer was calculated using the Spearman-Karber method (Spearman, C., "The Method of Right and Wrong Cases" ('Constant Stimuli') Without Gauss's Formula", *Br. J. Psychol.*, 1908;2:227-242) and indicates the quantity of virus which infects 50% of the tissue culture wells ($TCID_{50}$).

Cell-associated VSV was prepared by incubating a confluent monolayer of human A549 cells with 5 ml of $10^7$ $ID_{50}$/ml VSV in serum-free DMEM for 1 hour at 37° C. under 5% $CO_2$ in 150 $cm^2$ tissue culture flasks. The multiplicity of infection under these conditions was approximately 2.1 $TCID_{50}$/cell. After decanting off the liquid, the attached cells were washed three times to remove free virus with 50 ml PBS per wash. Afterwards, 40 ml of DMEM containing 5% FCS were added, and the cells were incubated for an additional 4¾ hours. The attached cells were washed three times with PBS and released by treatment for 10 minutes with a normal saline solution containing 0.01% trypsin (Cooper Biomedical, Freehold, New Jersey; two times crystallized) and 5 $\mu$g/ml EDTA. The released cells were collected by centrifugation, washed three times with PBS and resuspended in PBS.

To assess inactivation, cell-free virus was added to the blood component being studied at a 1:10 dilution, and 3 ml aliquots of this mixture were distributed in polystyrene tubes (Fisher Scientific, Springfield, New Jersey; Cat.#2027; 7 ml capacity) followed by the addition of the phthalocyanine derivative. The samples were mixed continuously using a hematology mixer (Fisher Scientific, Cat. #14-060-1) and photoirradiated with light from a Solar Simulator (Oriel Corp., Stratford, Connecticut) fitted with a Zenith 300 watt Xe short arc lamp equipped with an amber, 570 nm longpass filter (Oriel Corp.). The light power at the sample was about 25-26 mWatts/$cm^2$ as measured with a photometer (Model No. IL1350 International Light, Newburyport, Massachusetts) with a detector (Model No. SED038) fitted with a wide band pass filter (F#8174) and a diffuser (W#4425). As compared with the data presented below, the filtration through a 676 nm interference filter (the Optometrics Corp., Catalog No. 02-6765, Ayer, MA) placed on the detector permitted the transmission of 1.3% of the light power. Irradiation times were typically 30, 60 and 120 minutes corresponding to fluences of 44, 88 and 176 J/$cm^2$ respectively. A constant flow of air was provided by a fan, and the temperature of the sample did not rise above 28° C. during irradiation.

Virus inactivation of an entire red blood cell concentrate (RBCC) unit was carried out in a 600 ml capacity #5J359 bag (Fenwall Division, Deerfield, Illinois). A Thermolyne Speci-mix mixer model M26125 (Sybron Corp., Iowa) was used to mix the sample in the bag during photoirradiation.

For assessment of virus inactivation, the reaction was stopped by 10-fold dilution into DMEM containing 5% fetal calf serum, and the red blood cells were removed by centrifugation at 1500 rpm for 10 minutes. The lack of virus inactivation at this dilution or in the absence of light was confirmed for each of the inactivation conditions studied. Samples were sterile filtered (Swinnex filters, Millipore Corp., Bedford, Massachusetts) and frozen at $-70°$ C. or below until assay.

The procedures for the assessment of the inactivation of cell-associated VSV were similar to those of cell-free VSV, except all experiments with cell-associated VSV were carried out under totally controlled aseptic conditions. At the conclusion of the experiment, the infected A549 cells were isolated with the addition of Ficoll-Paque (Pharmacia Fine Chemicals, Piscataway, New Jersey) and centrifuged in a swinging bucket rotor at 1800 xg for 30 minutes at ambient temperature. The layer containing the A549 cells was collected, washed three times with PBS by centrifugation, resuspended in 1 ml PBS and immediately assayed for VSV infectivity by endpoint, 10-fold serial dilutions as with cell-free virus.

Assessment of HIV Inactivation

The HTLV $III_b$ strain of human immunodeficiency virus (HIV) was used in these experiments. Measurement of infectivity was similar to that reported previously (Prince, A. M., Pascual, D., Kosolapov, L. B., et al, "Prevalence, Clinical Significance, and Strain Specificity of Neutralizing Antibody to the Human Immunodeficiency Virus", *The Journal of Infectious Diseases*, 1987;156:268-272). Ten thousand-fold concentrates of cell-free HIV, prepared by continuous flow sucrose banding, were purchased from Bionetics, Inc. (Rockville, M.D.). Titrations were carried out with serial, ten-fold dilutions in microtiter plates using RPMI 1640 containing 10% FCS, with either CEM or H9 cells at a concentration of $8 \times 10^5$/mL. Before use, cells were conditioned by incubation for 1 hour at 37° C. in the above medium containing 2 $\mu$g/mL of polybrene. Virus in treated samples was adsorbed to cells for 2 hours at 37° C. in the dark. Cultures were then washed twice in medium by centrifuging plates for 10 minutes at 2000 rpm and aspirating the supernatants in order to remove the treating compound and reduce toxicity. 150 $\mu$l cultures were then fed with 25 $\mu$l of medium at 4, 7 and 10 days. At 14 days, cultures were washed twice with PBS (phosphate buffered saline) to remove viral antigens carried over from the inoculum, and the cells were lysed in PBS containing 0.5% Triton X-100. Lysates were assayed for HIV p55 antigens by ELISA using plates coated with rabbit antiserum against recombinant p55 (Syntex Corp., Palo Alto, CA.) and peroxidase labeled rabbit anti-p55. This assay had essentially the same sensitivity in measurement of p24 as the Dupont p24 antigen assay.

To increase the sensitivity for measurement of small quantities of residual virus, 0.5-1.0 ml of undiluted virus-containing fluids treated with AlPc were also inoculated into 5 ml macro-cultures, and were fed by removing half volumes and replacing with fresh medium twice weekly for 4 weeks.

For cell-associated HIV, 25 ml culture of $8 \times 10^5$/mL CEM of H9 cells were inoculated with $10^4$ TCID$_{50}$ of HIV. Cultures were fed by removal of half volumes and replacement with fresh medium twice weekly. At each feeding, supernatant fluids were assayed for p55 antigens by ELISA. When the titer reached 1:64 or greater, usually at 10–12 days, the infected cells were used in the following experiments. Prior to use in experiments, aliquots of $10^6$ infected cells were pelleted and resuspended in 100 μL of HIV immune globulin (Prince, A. M., Horowitz, B., Baker, L. et al, "Failure of an HIV Immune Globulin To Protect Chimpanzees Against Experimental Challenge With HIV", PNAS, 1988;85:6944–6948), incubated for 1 hour at 37° C., and washed three times in culture medium in order to reduce the amount of non-cell associated virus. Infected cells were then suspended in medium, or whole blood anticoagulated with CPD (citrate phosphate dextrose), to a concentration of $10^6$/mL. These mixtures were exposed to varying concentrations of AlPc with or without exposure to light. After treatment, samples were diluted 1:2 with RPMI-1640 and centrifuged through Ficoll-Hypaque to separate lymphocytes from erythrocytes. The recovered lymphocytes were washed three times, counted, and serially diluted in 100 μl of medium. Uninfected CEM cells were then added and the cultures processed as for the infectivity titration described above.

Red Cell Measurements

Total hemoglobin was quantitated using Drabkin's reagent (Sigma Procedure No. 525, Sigma Diagnostics, St. Louis, Missouri). Plasma hemoglobin was assessed, after removal of cells by centrifugation, by measuring the optical density of the plasma at A540 and assuming an absorbance of 0.86 for a 1 mg/ml solution (Antonini, E. and Brunori, M., "Hemoglobn and Myoglobin in Their Reactions with Ligands", Amsterdam: North-Holland Publishing Co., 1971. (Neuberger A., Tatum E. L., eds., *Frontiers of Biology;* Vol. 21)). Prior to centrifugation, red cell concentrates were diluted 1:1 with PBS. The results were expressed as a percentage of the total hemoglobin present. Osmotic fragility of treated red blood cells was measured as previously described in Dacie, J. V., Lord, M. B., Vaughan, J. M. and Oxon, D. M., "The Fragility of Red Blood Cells, Its Measurements and Significance", *J. Path Bact.,* 1938, 46:341–356. pH measurements were made with a PHM 82 pH meter (Radiometer America Inc., Cleveland, Ohio).

EXAMPLE 1

Inactivation of VSV and EMC By AlPc

Figures 1A, 1B, 1C, 1D:
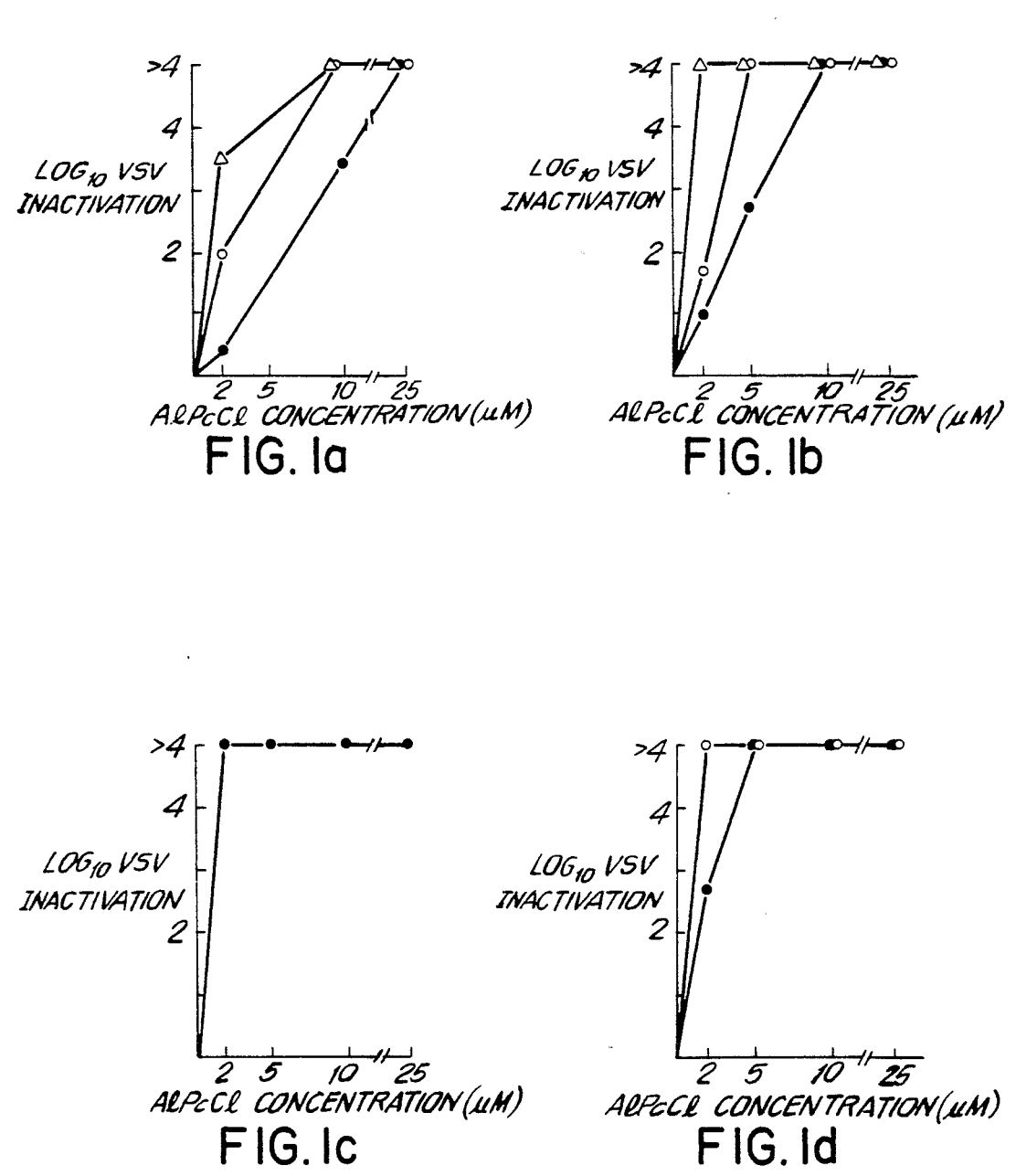

The inactivation of cell-free VSV added to whole blood ($5 \times 10^9$ red blood cells/ml) or a red cell concentrate ($1 \times 10^{10}$ red blood cells/ml) in the presence of AlPc was dependent on its concentration and the fluence (dosage) of light (FIG. 1). Cell-free VSV and AlPc at the indicated concentration were added to whole blood (FIG. 1a), a red blood cell concentrate (FIG. 1b), whole blood diluted 5-fold with PBS (FIG. 1c) and a red blood cell concentrate diluted 2-fold with PBS (FIG. 1d). The plasma protein concentration in whole blood and the red cell concentrate was 60 mg/mL prior to the dilution indicated. Samples (3 mL) were exposed to a constant intensity of light (25–26 mWatts/cm$^2$) for a varying duration such that the total light fluence was 44 J/cm$^2$ (closed circles), 88 J/cm$^2$ (open circles), or 176 J/cm$^2$ (open triangles). Following exposure to light, virus infectivity was assessed as described herein.

Complete inactivation of VSV ($\geq 10^{4.0}$ to $10^{4.5}$ TCID$_{50}$) added to whole blood was observed at an AlPc concentration of 10 μM and a light fluence of 88 and 176 J/cm$^2$, corresponding to a light intensity of 25 mwatts/cm$^2$ and exposure times of 60 and 120 minutes, respectively. At a fluence of 44 J/cm$^2$, complete inactivation of added VSV required an AlPc concentration of 25 μM (FIG. 1a). The inactivation of VSV added to a red blood cell concentrate (RBC concentration = $1 \times 10^{10}$/ml; FIG. 1b) was similar to that observed in whole blood (FIG. 1a). Complete inactivation of VSV added to whole blood first diluted 5-fold (FIG. 1c) or to a red blood cell concentrate first diluted 2-fold (FIG. 1d) with PBS occurred at a lower AlPc concentration for a given light fluence than that observed with their undiluted counterparts. VSV inactivation did not occur in the absence of AlPc or in the dark (data not shown).

Red blood cell integrity, as determined by hemoglobin released during the treatment period, was well maintained (lysis < 2%) under each of the conditions presented in FIG. 1.

Cell-free EMC, a non-enveloped virus, was not inactivated on treatment with AlPc when evaluated under conditions similar to those described above (data not shown).

EXAMPLE 2

Intracelluilar VSV was prepared as described hereinabove. Comparison of the concentration of cells harvested following trypsin treatment ($2.07 \times 10^7$/ml) to viral infectious units ($1 \times 10^6$ TCID$_{50}$/50 μl ; $2.0 \times 10^6$ TCID$_{50}$/ml) suggests that virtually every cell contained infectious virus. This intracellular VSV, added to a red blood cell concentrate, was completely inactivated ($\geq 10^{5.6}$ TCID$_{50}$) on treatment of this red cell concentrate with 10 μM AlPc and 88 J/cm$^2$ (Table I). Comparison with the results reported with cell-free virus (FIG. 1b) indicates that inactivation of the cell-associated form is more difficult. Red blood cell structure and function were unaffected.

TABLE I

| Inactivation of Intracellular VSV Added to a Red Cell Concentrate with AlPc | | | |
|---|---|---|---|
| AlPc Concentration (μM) | VSV Titer(log$_{10}$) | | Log$_{10}$ Kill |
| | Dark | Light* | |
| 0 | 5.2 | 5.1 | 0.0 |
| 0 | 5.0 | 3.6 | 1.5 |
| 2 | 5.1 | $\leq -0.5$ | $\geq 5.6$ |
| 5 | 5.3 | $\leq -0.5$ | $\geq 5.6$ |
| 10 | | | |
| | Av 5.1 | | |

*88 J/cm$^2$

EXAMPLE 3

The inactivation of cell-free VSV in the presence of the di- and tetra-sulfonated derivatives of AlPc was also examined. Cell-free VSV and AlPcS$_2$ (FIG. 2a and FIG. 2b) or AlPcS$_4$ (FIG. 2c and FIG. 2d) at the indicated concentration were added to whole blood (FIG.

Figure 2B:
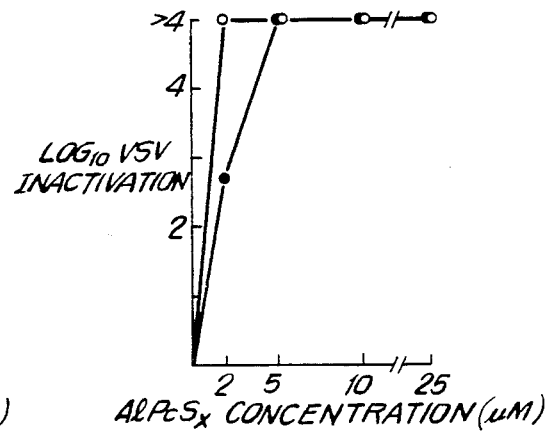
FIG. 2b depicts the results using AlPcS$_2$ with a red blood cell concentrate.
Figure 2C:
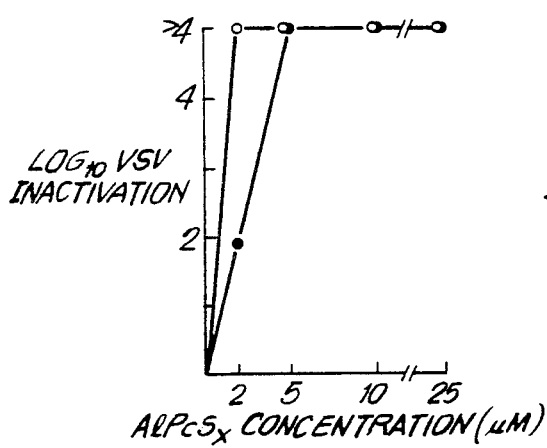
FIG. 2c depicts the results using AlPcS$_4$ with whole blood.
Figure 2D:
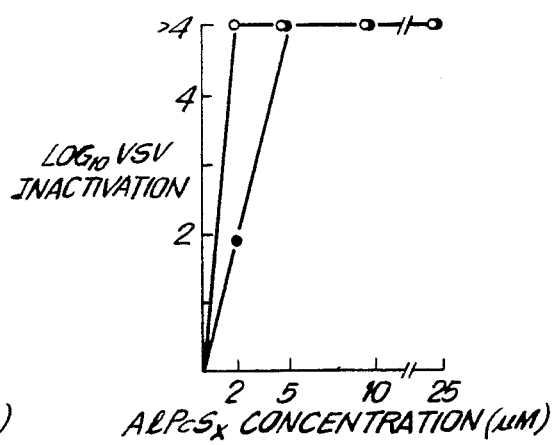
FIG. 2d depicts the results using AlPcS$_4$ with a red blood cell concentrate.

2a and FIG. 2c) or a red blood cell concentrate (FIG. 2b and FIG. 2d). Other details are as described above with respect to FIG. 1. Complete inactivation ($\geq 10^4$ TCID$_{50}$) of VSV with the sulfonated derivatives occurred at a lower AlPc concentration for a given light fluence than that observed with the non-sulfonated form (FIG. 1 vs. FIG. 2). Complete inactivation of VSV added to either whole blood diluted 5-fold or a red cell concentrate diluted 2-fold with PBS was observed with 2 μM of either sulfonated derivative and a light fluence of 44 J/cm$^2$ data not shown). With regard to hemoglobin release during the course of treatment, little ($\leq 2\%$) was observed at AlPcS$_x$ concentrations up to 25 μM and a light fluence up to 176 J/cm$^2$ (Table II).

TABLE II

Percent Hempglobin Released on Treatment of
A Red Cell Concentrate with AlPc Derivatives

| AlPc Derivative | Light Fluence (J/cm$^2$) | Percent Hemoglobin Released AlPc conc: | | |
|---|---|---|---|---|
| | | 5 μm | 10 μM | 25 μM |
| AlPc | 88 | 1.1 | 0.8 | 1.1 |
| | 176 | 1.5 | 0.9 | 1.4 |
| AlPcS$_2$ | 88 | 0.6 | 0.5 | 0.3 |
| | 176 | 0.6 | 0.5 | 0.4 |
| AlPcS$_4$ | 88 | 0.2 | 0.5 | 0.3 |
| | 176 | 0.3 | 0.5 | 0.3 |

EXAMPLE 4

Inactivation of HIV By AlPc

HIV in either a cell-free or intracellular form was added to either whole blood or a red cell concentrate in a test tube. Treatment of cell-free HIV used 10 μM AlPc and 176 J/cm$^2$; treatment of intracellular HIV used 5 μM AlPc and 44 J/cm$^2$. At the conclusion of treatment, the samples were processed as described above and HIV antigen measurements were made.

Treatment of whole blood or a red cell concentrate with AlPc was shown to inactivate $\geq 10^{4.2}$TCID$_{50}$ of cell-free $\leq 10^{3.6}$TCID$_{50}$ of a intracellular HIV (Table III). Red blood cell structure and functions were unaffected.

TABLE III

| INACTIVATION OF HIV | | |
|---|---|---|
| | Log$_{10}$ Inactivation | |
| | Cell-Free | Intracellular |
| Whole Blood | $\geq 4.2$ | $\geq 3.6$ |
| Red Cell Concentrate | $\geq 4.2$ | not done |

EXAMPLE 5

Red Blood Cell Integrity

Typical results of the percent hemoglobin released from red blood cells during the course of treatment with AlPc derivatives are given in Table II. The percent released varied between 0.2% and 1.5% of the total hemoglobin present.

Figure 3:
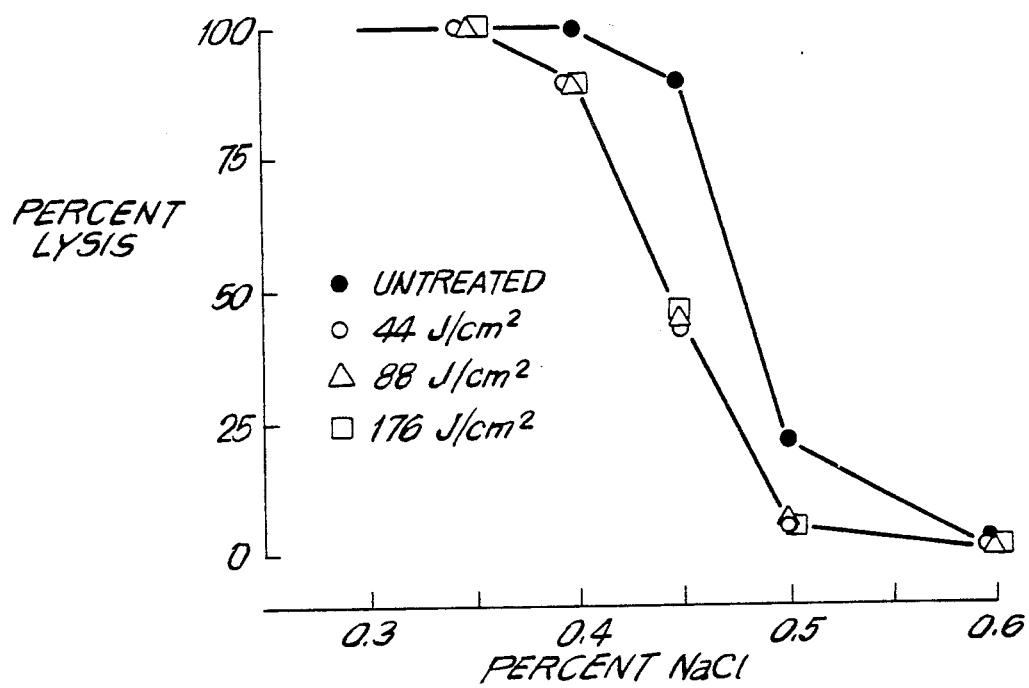
FIG. 3 is a graph depicting erythrocyte osmotic fragility prior to and following treatment with AlPc.

The erythrocyte osmotic fragility following treatment of whole blood was measured with no prior removal of AlPc (FIG. 3). Whole blood was treated with 10 μM AlPcCl and a light fluence of 44 J/cm$^2$ (open circles), 88 J/cm$^2$ (open triangles) and 176 J/cm$^2$ (open squares). Following treatment and with no subsequent processing, the erythrocyte osmotic fragility was determined in these samples and in the untreated control (closed circles) by dilution into solutions of saline at the indicated concentration. Following incubation for 30 minutes and centrifugation, released hemoglobin was measured with Drabkin's solution and compared with that released on dilution into distilled water.

As compared with the untreated control, treatment with 10 μM AlPc at light fluences of 44, 88 and 176 J/cm$^2$ increased the resistance of the red cells to osmotic shock.

EXAMPLE 6

To evaluate the storage stability of treated red cells, 3 ml of whole blood were treated with 10 μM AlPc and a light fluence of 176 J/cm$^2$, as in Example 1. Following a storage period of 17 days, released hemoglobin was 1.8% of the total and the pH of the sample was 6.9, indicative of excellent storage compatibility.

EXAMPLE 7

A study of VSV inactivation in an intact red cell consecrate unit was conducted. A red cell concentrate contained in a Fenwal 5J359 blood bag was illuminated from one side only. The inactivation of all detectable cell-free VSV ($\geq 10^{4.5}$ TCID$_{50}$) was achieved with 10.5 μM AlPc and a light fluence of 264 J/cm$^2$ corresponding to a treatment duration of 3 hours (Table IV). A 10-fold more sensitive macroculture assay did not show the presence of VSV (kill $\geq 10^{5.5}$ TCID$_{50}$) at 352 and 396 J/cm$^2$. Less than 2% lysis was observed even at 396 J/cm$^2$.

TABLE IV

Inactivation of Cell-Free VSV Added to An
Individual Red Cell Concentrate Unit

| AlPc Concentration (μM) | Light Fluence (J/cm$^2$) | VSV Titer (log$_{10}$ TCID$_{50}$) |
|---|---|---|
| 0 | 0 | 4.0 |
| 10.5 | 88 | 2.8 |
| 10.5 | 176 | 1.3 |
| 10.5 | 264 | $\leq -0.5$ |
| 10.5 | 352 | $\leq -0.5$ |
| 10.5 | 396 | $\leq -0.5$ |

EXAMPLE 8

An assessment of the effect of phthalocyanine treatment on platelet function was conducted. Zinc phthalocyanine (ZnPc) in dimethylformamide was added to a platelet concentrate containing 5.36×10$^9$ platelets/mL and a plasma protein concentration of 60 mg/mL. The final concentration of ZnPc was 20 μM. At the indicated times, platelet count was determined, platelet morphology was assessed by measurement of mean volumes, and the ability of platelets to aggregate on addition of adenosine diphosphate (ADP) was assessed (Table V). Through the total treatment time, platelet count was maintained to the extent of 86%-91%. The mean volume of the platelets was unaffected. Aggregation in response to ADP, expressed either in terms of the initial rate of aggregation or the extent of aggregation was unchanged as compared with the DMF only control for 10 minute light exposure, though somewhat decreased for 15 and 30 minute light exposures.

TABLE V

Effect of Zinc Phthalocyanine on Platelets

| Sample | Platelet Count ($\times 10^{-9}$/mL) | Mean Platelet Volume (micron$^3$) | Aggregation Response Initial Rate ($\Delta$A/min) | Aggregation Response Maximum Extent ($\Delta$A) |
|---|---|---|---|---|
| Controls | | | | |
| No light, no ZnPc | 5.36 | 6.1 | 38 | 45 |
| Solvent (DMF) only | 5.65 | 6.4 | 34 | 26 |
| Test | | | | |
| ZnPc + 10 minute light | 4.74 | 6.3 | 35 | 28 |
| ZnPc + 15 minute light | 4.87 | 6.1 | 25 | 22 |
| ZnPc + 30 minute light | 4.63 | 5.8 | 25 | 20 |

EXAMPLE 9

Human red blood cells were washed twice with phosphate buffered saline to remove plasma and then diluted to the indicated concentration. Aluminum phthalocyanine tetrasulfonate (10 µM) was added to each and the samples irradiated as described above with 88 J/cm$^2$. Following irradiation, the degree of lysis was determined by the amount of hemoglobin released. As shown in Table VI, 100% lysis was observed with a red cell concentration of $4.5 \times 10^8$ cells/ml, but improved suddenly when the cell concentration was raised to $2.25 \times 10^9$ cells/ml or higher.

TABLE VI

Percent Hemolysis As a Function of Red Cell Concentration

| Red Cell Conc (cells/ml) | Percent Hemolysis |
|---|---|
| $9 \times 10^9$ | 2.9 |
| $4.5 \times 10^9$ | 2.9 |
| $2.25 \times 10^9$ | 2.7 |
| $4.5 \times 10^8$ | 100 |

EXAMPLE 10

Comparison Of Virus Kill Of Aluminum Phthalocyanine With Hematoporphyrin Derivative Vesicular stomatitis virus (VSV) was added to whole blood followed by either hematoporphyrin derivative (HPD), a dye with an absorbtion maximum below 630 nm, or aluminum phthalocyanine sulfonate. Each was exposed to light as above. The results (Table VII below) indicate that virus kill is both faster and more complete with AlPcS$_4$ than with HPD.

TABLE VII

| Compound | Conc (µM) | VSV Kill (log$_{10}$) 30 min | VSV Kill (log$_{10}$) 120 min |
|---|---|---|---|
| HPD* | 18 | 1.3 | 1.4 |
|  | 36 | 1.4 | 2.4 |
|  | 54 | 1.7 | 4.0 |
| AlPcS$_4$ | 5 | $\geq 4.0$ | $\geq 4.0$ |

*Assumed MW of 1106

It will be appreciated that the instant specification is set forth by way of illustration and not limitation, and that various modifications and changes may be made without departing from the spirit and scope of the present invention.

What is claimed is:

1. A process for treating a blood cell-containing composition in order to inactivate any extracellular lipid enveloped human pathogenic virus and intracellular human pathogenic virus contained therein without incurring substantial disruption or inactivation of the cells, comprising contacting the cell-containing composition having $\geq 1 \times 10^9$ cells/ml with a virucidally effective amount of at least one photodynamically active compound having an absorption maximum of $\geq 630$ nm, with light and with oxygen to substantially inactivate said virus if present therein and to effect a virus kill of at least 10$^4$ and to result in a retention of intact cell functionality and structure of greater than 80%.

2. A process according to claim 1, wherein intracellular virus is inactivated.

3. A process according to claim 1, wherein extracellular lipid enveloped virus is inactivated.

4. A process according to claim 1, wherein the cell-containing composition has 24 $5 \times 10^9$ cells/ml 5. A process according to claim 1, wherein the cell-containing composition has $\geq 1 \times 10^{10}$ cells/ml.

6. A process according to claim 1, wherein the cell-containing composition has >4 mg/ml protein.

7. A process according to claim 1, wherein the cell-containing composition has >25 mg/ml protein.

8. A process according to clam 1, wherein the cell-containing composition has 50 to 60 mg/ml protein.

9. A process according to claim 1, wherein the cells are unwashed cells.

10. A process according to claim 1, wherein the cells are unwashed and the cell-containing composition has $\geq 5 \times 10^9$ cells/ml.

11. A process according to claim 1, wherein the photoreactive compound is a phthalocyanine.

12. A process according to claim 11, wherein the phthalocyanine is an aluminum phthalocyanine.

13. A process according to claim 12, wherein the aluminum phthalocyanine is aluminum phthalocyanine chloride.

14. A process according to claim 12, wherein the phthalocyanine is a sulfonated form of aluminum phthalocyanine.

15. A process according to claim 14, wherein the phthalocyanine is AlPcS$_2$ or AlPcSp$_4$.

16. A process according to claim 1, wherein the retention of intact cell functionality and structure is greater than 90%.

17. A process according to claim 1, wherein the retention of intact cell functionality and structure is greater than 98%.

18. A process according to claim 1, wherein at least 10$^6$ infectious units of virus are inactivated.

19. A process according to claim 1, further comprising storing the resultant treated cell-containing composition in liquid or frozen form, whereby reduced cell destruction is obtained.

20. A process according to claim 1, wherein the cell-containing composition contains red blood cells.

21. A process according to claim 20, wherein the red blood cells are treated in a blood bag.

* * * * *